(12) United States Patent
Choi (10) Patent No.: US 6,952,614 B2
(45) Date of Patent: Oct. 4, 2005

(54) BED TYPE HOT COMPRESS AND ACUPRESSURE APPARATUS AND A METHOD OF CONTROLLING IT

(75) Inventor: Sang Ui Choi, Chungcheongnam-do (KR)

(73) Assignee: Ceragem Co., Ltd., Seoul (KR)

( * ) Notice: Subject to any disclaimer, the term of this patent is extended or adjusted under 35 U.S.C. 154(b) by 80 days.

(21) Appl. No.: 10/757,436

(22) Filed: Jan. 15, 2004

(65) Prior Publication Data

US 2005/0065580 A1 Mar. 24, 2005

(30) Foreign Application Priority Data

Aug. 13, 2003 (KR) .................................... 2003-0055923

(51) Int. Cl.⁷ ................................................. A61F 7/12
(52) U.S. Cl. ......................... 607/98; 607/100; 607/96; 601/19; 601/20
(58) Field of Search ........................... 607/96, 98, 100, 607/154, 156; 601/19, 20; 606/201, 204, 237–245

(56) References Cited

U.S. PATENT DOCUMENTS

| | | | |
|---|---|---|---|
| 3,645,256 A | * | 2/1972 | Morrison .................... 601/122 |
| 5,094,225 A | * | 3/1992 | Craw .......................... 601/19 |
| 6,591,141 B2 | | 7/2003 | Lee |
| 6,606,520 B1 | * | 8/2003 | Lee ............................ 607/98 |
| 2004/0158176 A1 | * | 8/2004 | Park ........................... 601/18 |

FOREIGN PATENT DOCUMENTS

| | | |
|---|---|---|
| KR | 1999-26999 | 5/2000 |
| KR | 2000-11259 | 9/2000 |
| KR | 2001-10766 | 10/2000 |
| KR | 2000-0007031 | 9/2002 |
| KR | 2001-20113 | 10/2002 |

* cited by examiner

Primary Examiner—Roy D. Gibson
(74) Attorney, Agent, or Firm—Greenblum & Bernstein, P.L.C.

(57) ABSTRACT

The present invention provides a bed type hot compress and acupressure apparatus using a means for controlling a location of a hyperthermo-radiative device wherein a moving location of the hyperthermo-radiative device can be controlled based on an actually moved distance of the hyperthermo-radiative device. In the present invention, the means for controlling the location of the hyperthermo-radiative device comprises (a) a reciprocating unit including a belt gear for converting a rotational force of an electric-powered motor into a forward and rearward reciprocating motion, a belt member that is engaged and in contact with an outer peripheral surface of the belt gear and reciprocated forward or rearward, the hyperthermo-radiative device connected to the belt member to reciprocate forward and rearward, and a pulley; and (b) a signal sensor unit including a rotational shaft for directly transmitting the rotational force, a signal rotating plate rotated together with the belt gear by the rotational shaft, and a sensor member that is adjacent to both faces of the signal rotating plate to sense a signal from the signal rotating plate and transmit the sensed signal to a control unit. According to the present invention, since a moving distance of the hyperthermo-radiative device can be controlled using the means for controlling the location of the hyperthermo-radiative device on the order of millimeters, the hyperthermo-radiative device can be accurately located on the position of a vertebra input by a user, thereby enhancing the effects of treatment.

4 Claims, 5 Drawing Sheets

FIG 5 n : Number of through-holes
r : Radius of belt gear

FIG 6

BED TYPE HOT COMPRESS AND ACUPRESSURE APPARATUS AND A METHOD OF CONTROLLING IT

BACKGROUND OF THE INVENTION

1. Field of Invention

The present invention relates to a bed type hot compress and acupressure apparatus. More particularly, the present invention relates to a bed type hot compress and acupressure apparatus designed to accurately position a hyperthermo-radiative device at user's vertebral acupuncture points, and a method of controlling the hot compress and acupressure apparatus.

2. Description of the Prior Art

Generally, a conventional box type hot compress and acupressure apparatus was improved into a mat type hot compress and acupressure apparatus that in turn has been improved into a bed type hot compress and acupressure apparatus. The bed type hot compress and acupressure apparatus has a bed type frame as a basic structure on which a mat can be mounted. Further, in the bed type hot compress and acupressure apparatus, a hyperthermo-radiative device is mounted and reciprocated in a predetermined range within the mat. Typical bed type hot compress and acupressure apparatuses are disclosed in Korean Utility Model Patent Application No. 1999-26999, Korean Patent Application No. 2000-7031, Korean Utility Model Patent Application No. 2000-11259 and U.S. patent application Ser. No. 09/990, 861. The typical bed type hot compress and acupressure apparatus is also called as a mat for hot compress and acupressure in Korea.

Each of such bed type hot compress and acupressure apparatuses has an advantage in that a vertebra region of a user who lies on the mat can be hyper thermally treated according to a program stored in a control box of the apparatus. Thus, such bed type hot compress and acupressure apparatuses have been used widely. In conventional bed type hot compress and acupressure apparatuses, rails necessary for reciprocation of a hyperthermo-radiative device are made in the form of a gentle curve, a marginal space is flexibly provided to a certain extent in a predetermined range when the hyperthermo-radiative device is reciprocated, or a predetermined resilient spring is mounted in the hyperthermo-radiative device.

Meanwhile, in the bed type hot compress and acupressure apparatuses used widely nowadays, the movement of the hyperthermo-radiative device that has influence directly on hyperthermic treatment for users' vertebrae is controlled by an automatic program. However, such a control method is performed on the basis of a predetermined period of time. In other words, the conventional bed type hot compress and acupressure apparatuses which have been used heretofore are set such that their hyperthermo-radiative devices are moved in accordance with the passage of time based on conditions that have been input through remote controls by users.

However, since the conventional bed type hot compress and acupressure apparatus is controlled with the passage of time regardless of an actually moved distance of the hyperthermo-radiative device, there is a difference in the moved distance of the hyperthermo-radiative device between a case where a great deal of overload per unit time is exerted on the hyperthermo-radiative device and a case where no overload is exerted thereon.

Therefore, the conventional bed type hot compress and acupressure apparatus has a disadvantage in that when a user wants to be hyper thermally treated on his specific region, a final location of a hyperthermo-radiative device of the apparatus may vary according to the amount of overload exerted thereon, and thus, uniform and equal effects of hyperthermic treatment cannot be obtained sufficiently under the same conditions. This is an inevitable disadvantage in the conventional bed type hot compress and acupressure apparatus that controls the movement of the hyperthermo-radiative device based on time.

SUMMARY OF THE INVENTION

Accordingly, the present invention is conceived to solve the problems in the prior art. An object of the present invention is to provide a bed type hot compress and acupressure apparatus, wherein a moving location of a hyperthermo-radiative device is controlled based on a distance by which the hyperthermo-radiative device has been actually moved, regardless of the passage of time.

Another object of the present invention is to provide a method of controlling a hot compress and acupressure apparatus, wherein a hyperthermo-radiative device can be accurately located at a desired region of user's vertebrae to be hyper thermally treated by controlling a location of the hyperthermo-radiative device.

The present invention provides a bed type hot compress and acupressure apparatus, wherein a moving location of a hyperthermo-radiative device is controlled based on a distance by which the hyperthermo-radiative device has been actually moved, regardless of the passage of time.

The bed type hot compress and acupressure apparatus according to the present invention comprises (a) a bed frame that defines an entire shape of the apparatus and has members to be assembled with one another; (b) a main mat and an auxiliary mat placed and mounted on the bed frame; (c) two curved rails mounted at a central portion within the main mat; (d) a means for controlling a location of the hyperthermo-radiative device such that a moving distance of the hyperthermo-radiative device can be controlled based on an actually moved distance thereof regardless of the passage of time; and (e) a control unit for allowing the user to arbitrarily control the means for reciprocating the hyperthermo-radiative device.

In the present invention, the means for controlling a location of the hyperthermo-radiative device comprises (i) a reciprocating unit including a belt gear coupled to a motor shaft of an electric-powered motor to convert a rotational force of the electric-powered motor into a forward and rearward reciprocating motion, a belt member that is engaged and in contact with an outer peripheral surface of the belt gear and reciprocated forward or rearward by means of the belt gear, the hyperthermo-radiative device connected to the belt member to reciprocate forward and rearward, and a pulley disposed on a side opposite to the belt gear to reciprocate the belt member; and (ii) a signal sensor unit including a rotational shaft connected to the motor shaft and the belt gear to directly transmit the rotational force, a signal rotating plate rotated together with the belt gear by the rotational shaft, and a sensor member that is adjacent to both faces of the signal rotating plate to sense a signal from the signal rotating plate and transmit the sensed signal to a control unit.

Further, the present invention provides a method of controlling a bed type hot compress and acupressure apparatus, wherein a hyperthermo-radiative device of the apparatus is reciprocated and the reciprocating motion is controlled based on a moving distance of a belt member by using the means for controlling the location of the hyperthermo-radiative device. In the method of controlling a location of the bed type hot compress and acupressure apparatus according to the present invention, a control method performed by the means for controlling the location of the hyperthermo-radiative device comprises steps of (a) comparing a current location of the hyperthermo-radiative device with the position of the vertebra input by the user, and determining a direction in which the hyperthermo-radiative device should be moved; (b) moving the hyperthermo-radiative device by means of the electric-powered motor; (c) measuring, by the signal sensor unit, a location to which the hyperthermo-radiative device is actually moved, during the movement of the hyperthermo-radiative device, and comparing the actually moved location of the hyperthermo-radiative device with the position designated by the user; (d) performing continuously step (c) if the actually moved location of the hyperthermo-radiative device differs from the set position designated by the user; and (e) stopping the movement of the hyperthermo-radiative device and performing the hyperthermic treatment if the location and position are identical to each other.

BRIEF DESCRIPTION OF THE DRAWINGS

The above and other objects, features and advantages of the present invention will become apparent from the following description of preferred embodiments given in conjunction with the accompanying drawings, in which.

DETAILED DESCRIPTION OF THE PREFERRED EMBODIMENTS

Hereinafter, a bed type hot compress and acupressure apparatus using a means for controlling a location of a hyperthermo-radiative device and a method of controlling the bed type hot compress and acupressure apparatus according to the present invention will be described in detail with reference to the accompanying drawings. It will be apparent that the accompanying drawings are merely provided for the purpose of easy understanding of the technical features of the invention by those skilled in the art.

Figure 1:
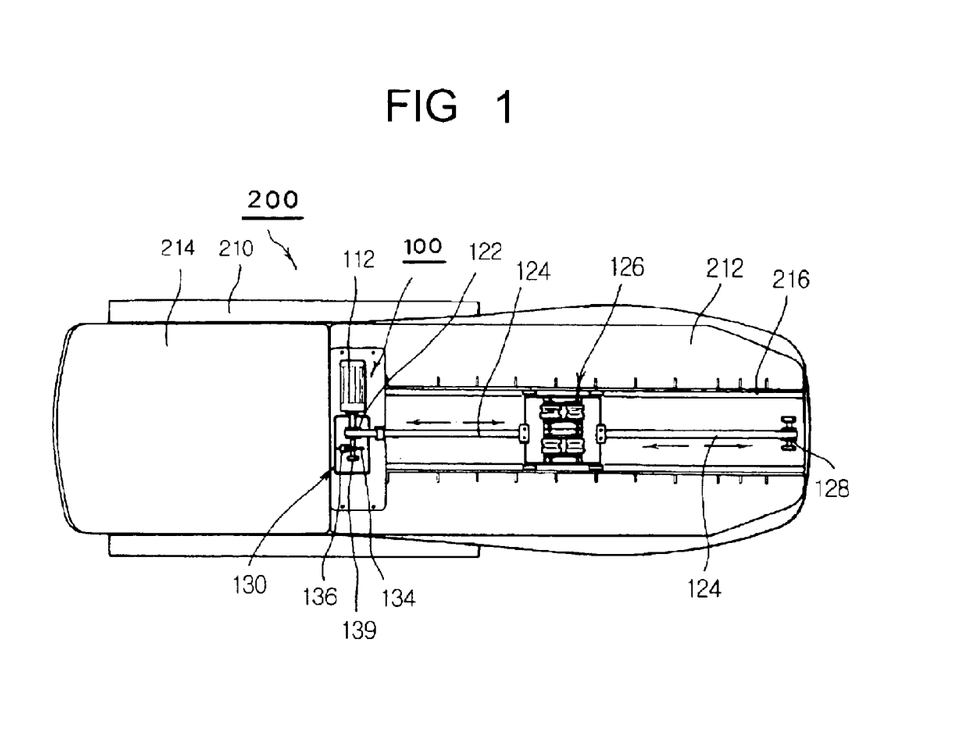
FIG. 1 is a plan view schematically showing a bed type hot compress and acupressure apparatus according to the present invention.
Figure 2:
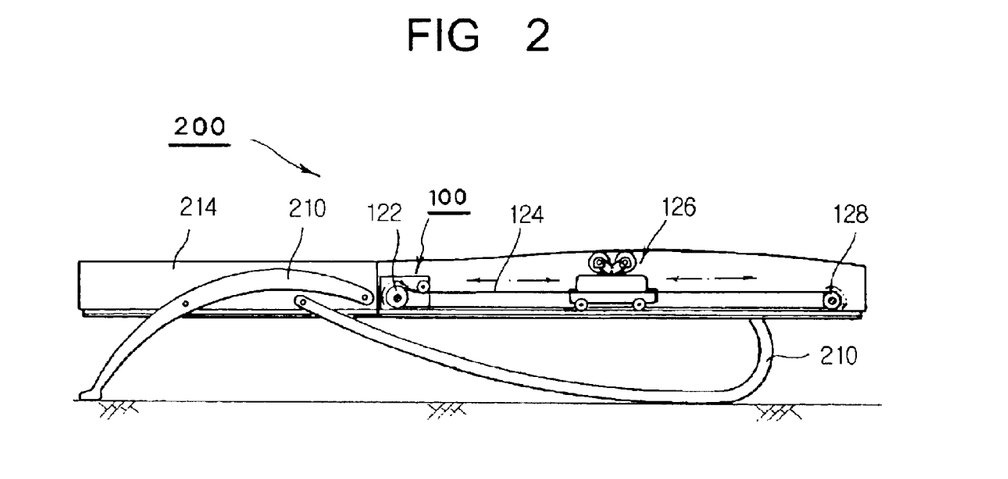
FIG. 2 is a side view schematically showing the bed type hot compress and acupressure apparatus according to the present invention.

FIG. 1 and FIG. 2 are a plan view and a side view schematically showing the bed type hot compress and acupressure apparatus 200 according to the present invention, respectively.

The bed type hot compress and acupressure apparatus 200 according to present invention comprises a bed frame 210 that defines an entire shape of the apparatus and has members to be assembled with one another. The bed type hot compress and acupressure apparatus 200 according to present invention comprises a main mat 212 and an auxiliary mat 214 which can be placed and mounted on the bed frame 210. The main mat 212 has an empty space at a center portion thereof, and two curved rails 216 are installed in the empty space. A hyperthermo-radiative device 126 is mounted on the curved rails 216 to reciprocate forward and rearward thereon.

The bed type hot compress and acupressure apparatus 200 according to present invention comprises a remote control (not shown) which allows a user to arbitrarily control the hyperthermo-radiative device 126, and a control unit (not shown) for automatically operating the hyperthermo-radiative device 126 according to a predetermined program. In the present invention, since the remote control and the control unit are identical to those of conventional elements, a detailed description thereof will be omitted.

The bed type hot compress and acupressure apparatus 200 according to present invention comprises a means 100 for controlling a location of the hyperthermo-radiative device. The bed type hot compress and acupressure apparatus 200 according to present invention is characterized in that the means 100 for controlling a location of the hyperthermo-radiative device described above is used. The means 100 for controlling a location of the hyperthermo-radiative device will be described in detail below.

Figure 3:
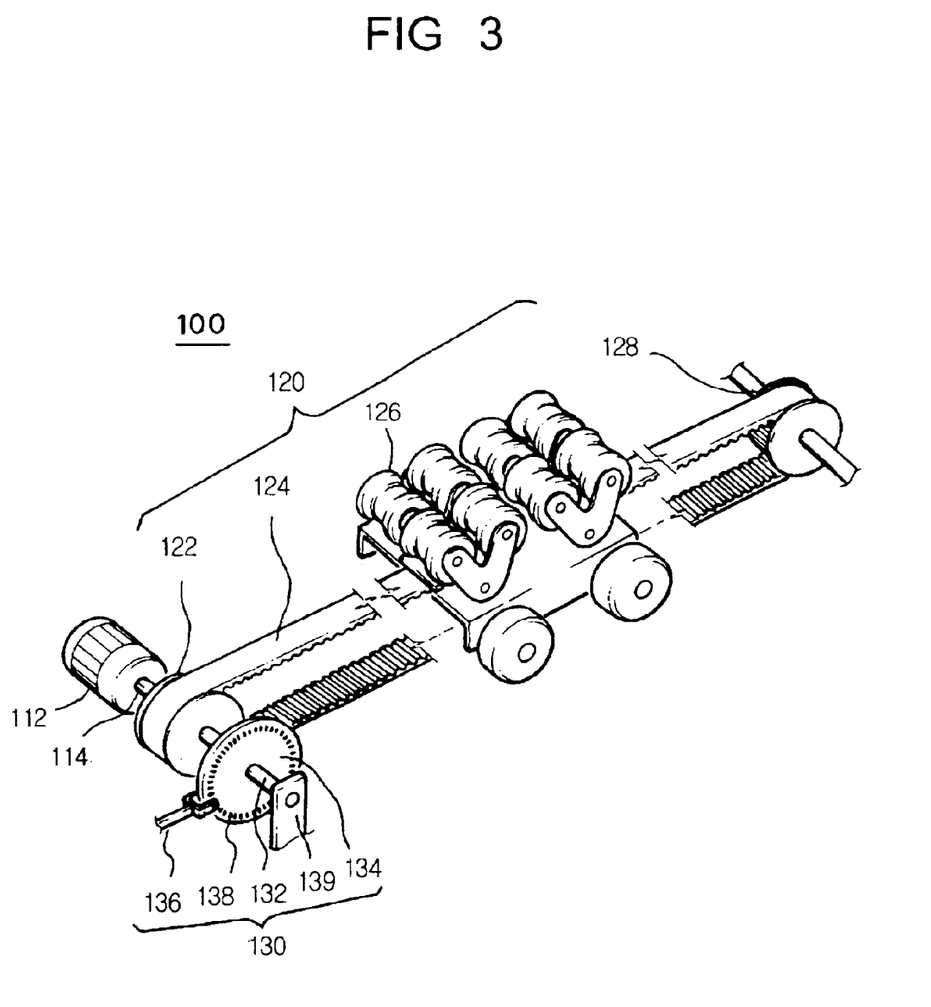
FIG. 3 is a conceptual view schematically showing a means for controlling a location of a hyperthermo-radiative device.

FIG. 3 is a conceptual view schematically showing a main portion of a hot compress and acupressure apparatus mounted with the means 100 for controlling a location of the hyperthermo-radiative device.

The means 100 for controlling a location of the hyperthermo-radiative device comprises a reciprocating unit 120 in which the movement of the hyperthermo-radiative device 126 thereof is determined by a control unit (not shown). In the present invention, the reciprocating unit 120 comprises a belt gear 122 for receiving a rotational force generated by an electric-powered motor 112 and then converting it into a forward and rearward reciprocating motion. At this time, the belt gear 122 is mechanically connected to the electric-powered motor 112 for generating the rotational force in response to a control signal from the control unit and a motor shaft 114 for transmitting the rotational force generated by the electric-powered motor 112. The belt gear 122 is employed to accurately and precisely convert the rotational force generated by the electric-powered motor 112 into the forward and rearward reciprocating motion. A belt member 124 is engaged and in contact with an outer peripheral surface of the belt gear 122. One end of the belt member 124 is connected to one side of the hyperthermo-radiative device 126 for performing hyperthermic treatment for user's vertebrae, and the other end thereof is connected to the other side of the hyperthermo-radiative device 126. The belt member 124 transmits the forward and rearward reciprocating motion converted by the belt gear 122 to the hyperthermo-radiative device 126. Although a conventional rubber belt, chain, or timing belt may be used as the belt gear 122, it is most desirable to use the timing belt. The hyperthermo-radiative device 126 is also called as a hot compress and acupressure treatment element in Korea, and may be replaced with a massage device or the like, if necessary. In the present invention, the reciprocating unit 120 comprises a pulley 128 disposed on a side opposite to the belt gear 122 to reciprocate the belt member 124.

Further, the means 100 for controlling a location of the hyperthermo-radiative device comprises a signal sensor unit 130 capable of controlling a substantial moving distance of the belt member 124 according to the amount of rotation of the electric-powered motor 112. The signal sensor unit 130 comprises a rotational shaft 132 connected to the motor shaft 114 and the belt gear 122 to transmit the rotational force as it is. The rotational shaft 132 receives the rotational force generated by the electric-power motor 112 to simultaneously rotate both the belt gear 122 and a signal rotating plate 134 while allowing the belt gear 122 and the signal rotating plate 134 to rotate about the same axis through the same rotating angle on concentric circles. A plurality of through-holes 138 are formed along a circumferential portion inside of an outer periphery of the signal rotating plate 134 therethrough (see FIG. 4). The through-holes 138 serve as passages through which a signal generated by a sensor member 136 disposed outside thereof can pass. Such a function of the through-holes 138 causes the signal rotating plate 134 to be continuously rotated or stopped, thereby controlling the rotation of the signal rotating plate 134. Since the number of the through-holes 138 is a parameter that determines the amounts of the forward and rearward motions of the belt gear 122 and the belt member 124, it is desirable to form the through-holes as many as possible.

In the present invention, the signal sensor unit 130 comprises the sensor member 136 that is adjacent to both faces of the signal rotating plate 134. The sensor member 136 functions to sense a signal passing through the through-holes 138 of the signal rotating plate 134 and transmit the signal to the control unit. To this end, the sensor member 136 comprises a signal emitting part 137a formed at one side portion extending from a body thereof and a signal sensing part 137b formed at the other side portion. Further, the signal sensor unit 130 comprises a support 139 for supporting the rotational shaft 132 at one end thereof.

Figure 4:
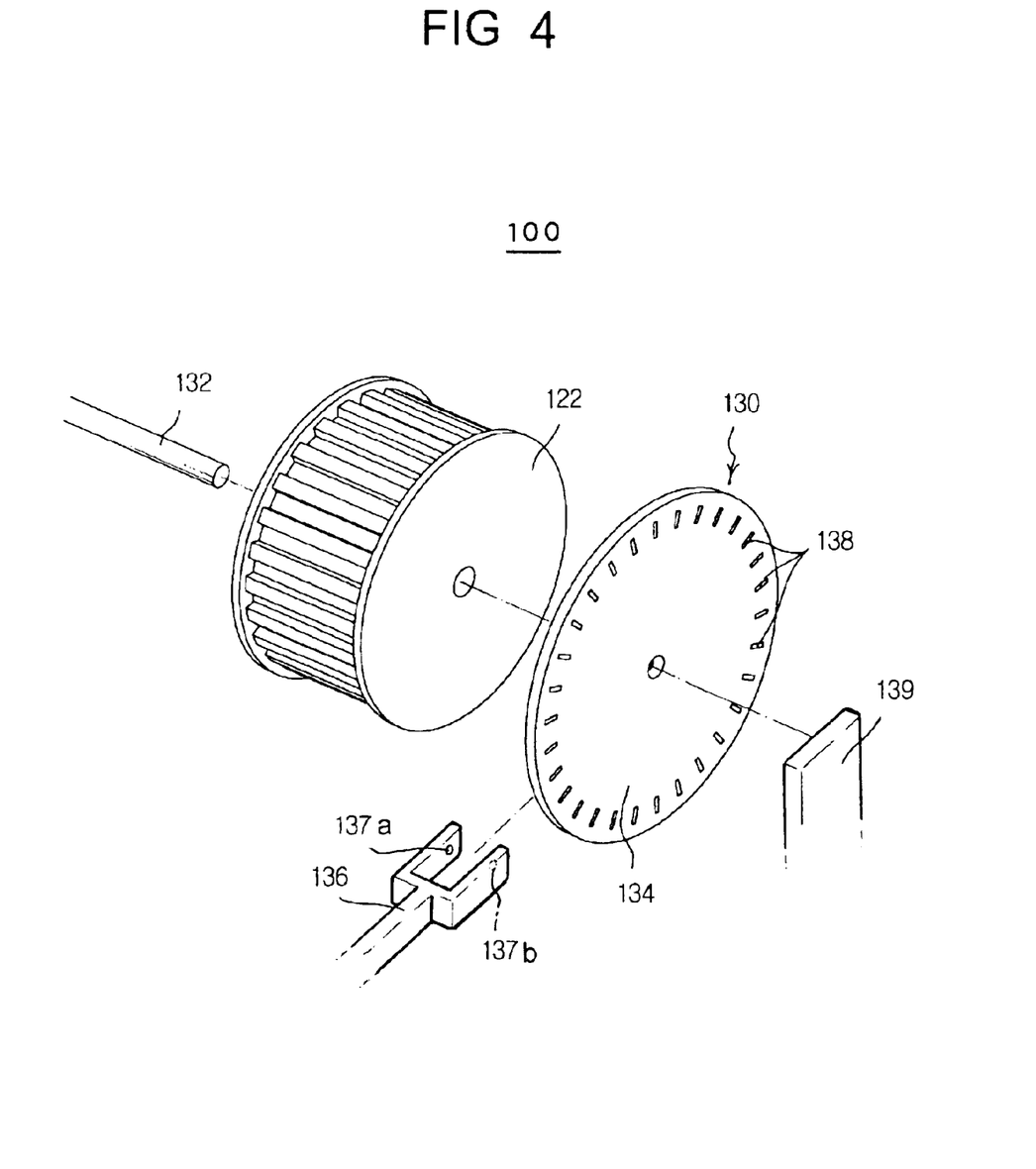
FIG. 4 is an exploded perspective view illustrating a cooperative relationship among main components of the means for controlling a location of the hyperthermo-radiative device.

FIG. 4 is an exploded perspective view conceptually showing a cooperative relationship among the belt gear 122, the signal rotating plate 134 and the sensor member 136 constituting a main part of the means 100 for controlling a location of the hyperthermo-radiative device.

In the present invention, when a user operates the electric-powered motor 112 using a remote control (not shown), a rotational force of the electric-powered motor 112 is transmitted to the belt gear 122 and the signal rotating plate 134 that in turn are rotated integrally. At this time, when the user inputs the position of his/her vertebra to be hyper thermally treated into the control unit, a distance from an actual location of the hyperthermo-radiative device 126 as a reference location to the position of the vertebra to be treated is calculated by a central process unit (CPU; not shown), and the calculated value is transmitted to the sensor member 136. Then, the signal emitting part 137a formed on one of the side portions of the sensor member 136 emits a predetermined signal to the signal rotating plate 134 that is continuously rotated during the operation of the electric-powered motor 112. At this time, the signal emitted from the signal emitting part 137a of the sensor member 136 passes through the through-holes 138 formed along the circumferential portion inside of the outer periphery of the signal rotating plate 134. The signal that has passed through the through-holes 138 is sensed by the signal sensing part 137b formed on the other of the side portions of the sensor member 136. On the contrary, portions of the signal rotating plate 134 between the respective though-holes 138 cut off the signal emitted by the signal emitting part 137a, so that the signal sensing part 137b cannot sense the emitted signal. Therefore, the number of revolutions of the signal rotating plate 134 and the belt gear 122 due to the rotation of the electric-powered motor 112 can be measured by means of the sensor member 136 and the through-holes 138 of the signal rotating plate 134. The number of revolutions is fed back into the control unit to find a position where the signal rotating plate 134 should be stopped.

With such a mechanism of the present invention, the belt gear 122 and the signal rotating plate 134 are rotated by the same number of revolutions through the same rotating angle as the electric-power motor 112 operates, and the belt gear 122 is stopped as soon as the signal rotating plate 134 is stopped.

Figure 5:
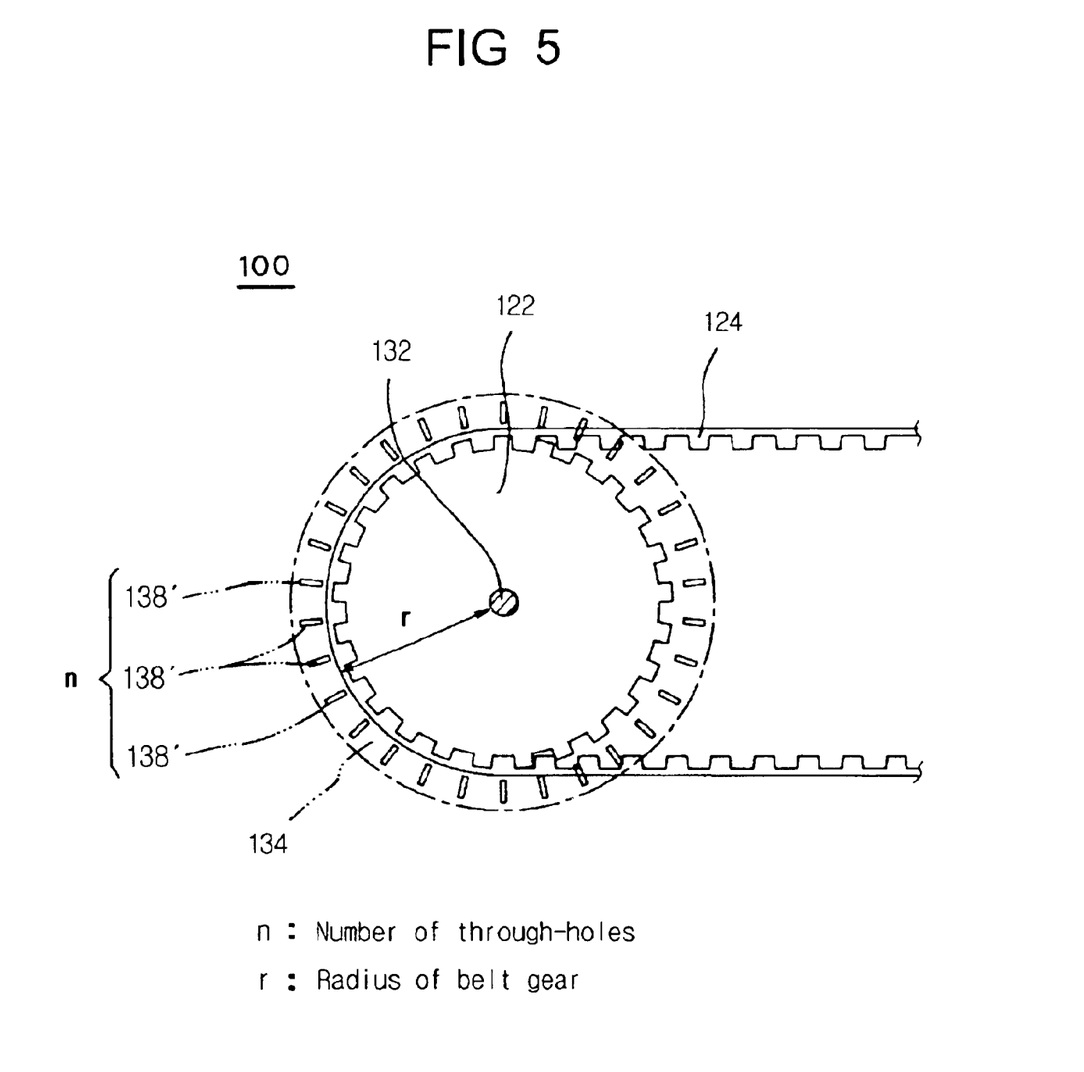
FIG. 5 is a conceptual view theoretically illustrating a method of controlling a location of the hyperthermo-radiative device by using the means for controlling a location of the hyperthermo-radiative device.

FIG. 5 is a conceptual view illustrating a cooperative relationship between the belt gear 122 and the signal rotating plate 134 in the means 100 for controlling a location of the hyperthermo-radiative device.

In FIG. 5, the belt member 124 is engaged with the outer peripheral surface of the belt gear 122, and the rotational shaft 132 serves as a central axis of both the belt gear 122 and the signal rotating plate 134. Thus, the belt gear 122 and the signal rotating plate 134 define concentric circles around the rotational shaft 132. Accordingly, even though the belt gear 122 and the signal rotating plate 134 have different radii, it is possible to assume that the plurality of the through-holes 138 formed along the circumferential portion inside of the outer periphery of the signal rotating plate 134 are formed on an outer periphery of the belt gear 122. In FIG. 5, imaginary through-holes 138' are indicated by imaginary lines outside of the outer periphery of the belt gear 122 in consideration of the cooperative relationship.

In FIG. 5, n imaginary through-holes 138' are formed outside of the outer periphery of the belt gear 122 and the radius of the belt gear 122 is r. At this time, the circumference of the belt gear 122 is $2\pi r$. Therefore, when the belt gear 122 is fully rotated once through 360 degrees, the angular distance is $2\pi r$, so that the belt member 124 is moved by $2\pi r$. Accordingly, when the signal rotating plate 134 is rotated by the electric-powered motor 112 through an angle between two adjacent through-holes 138, the belt gear 122 is rotated through an angle between two adjacent imaginary through-holes 138' so that the belt member 124 can be moved by $2\pi r/n$ forward or rearward.

This description can be summarized as follow:

The moving distance of the belt member 124 per rotation of the belt gear 122=$2\pi r$; and The moving distance of the belt member 124 per rotation through an angle between two adjacent through-holes 138= $2\pi r/n$.

As a more specific embodiment, a case where the number of the through-holes 138 formed in the signal rotating plate 134 is 100 and the radius of the belt gear 122 is 25 mm will be discussed as follows:

The number of revolutions of the signal rotating plate 134=The number of revolutions of the belt gear 122;

The moving distance of the belt member 124 per rotation of the signal rotating plate 134 (belt gear 122)=$2\pi \times 25$=157 mm; and The moving distance of the belt member 124 per rotation through an angle between two adjacent through-holes 138= $2\pi \times 25/100$ =1.57 mm.

Accordingly, when the belt gear 122 and the signal rotating plate 134 under the aforementioned conditions are used, the hyperthermo-radiative device 126 coupled to the belt member 124 can be controlled by a unit of 1.57 mm to a minimum. Further, in this case, since the actual moving distance of the hyperthermo-radiative device 126 is controlled based on only the moving distance of the belt member 124 even though time has passed considerably, the hyperthermo-radiative device 126 can be accurately operated regardless of the passage of time.

In the present invention, therefore, the hyperthermo-radiative device 126 can be exactly moved forward or rearward to the position where the user wants to be hyper thermally treated his/her vertebra.

When the user inputs information on the position of a vertebra required to be hyper thermally treated into the remote control, the control unit transmits the information to the electric-powered motor 112 so that the electric-powered motor 112 is rotated based on the information. The amount of rotation of the electric-powered motor 112 is controlled by the belt gear 122 and the belt member 124 on the order of millimeters. In the present invention, since other structural elements are identical to those of conventional bed type hot compress and acupressure apparatuses, a detailed description thereof will be omitted.

Moreover, the present invention provides a method of controlling the hyperthermo-radiative device of the bed type hot compress and acupressure apparatus based on the moving distance of the belt member using the means 100 for controlling a location of the hyperthermo-radiative device.

Figure 6:
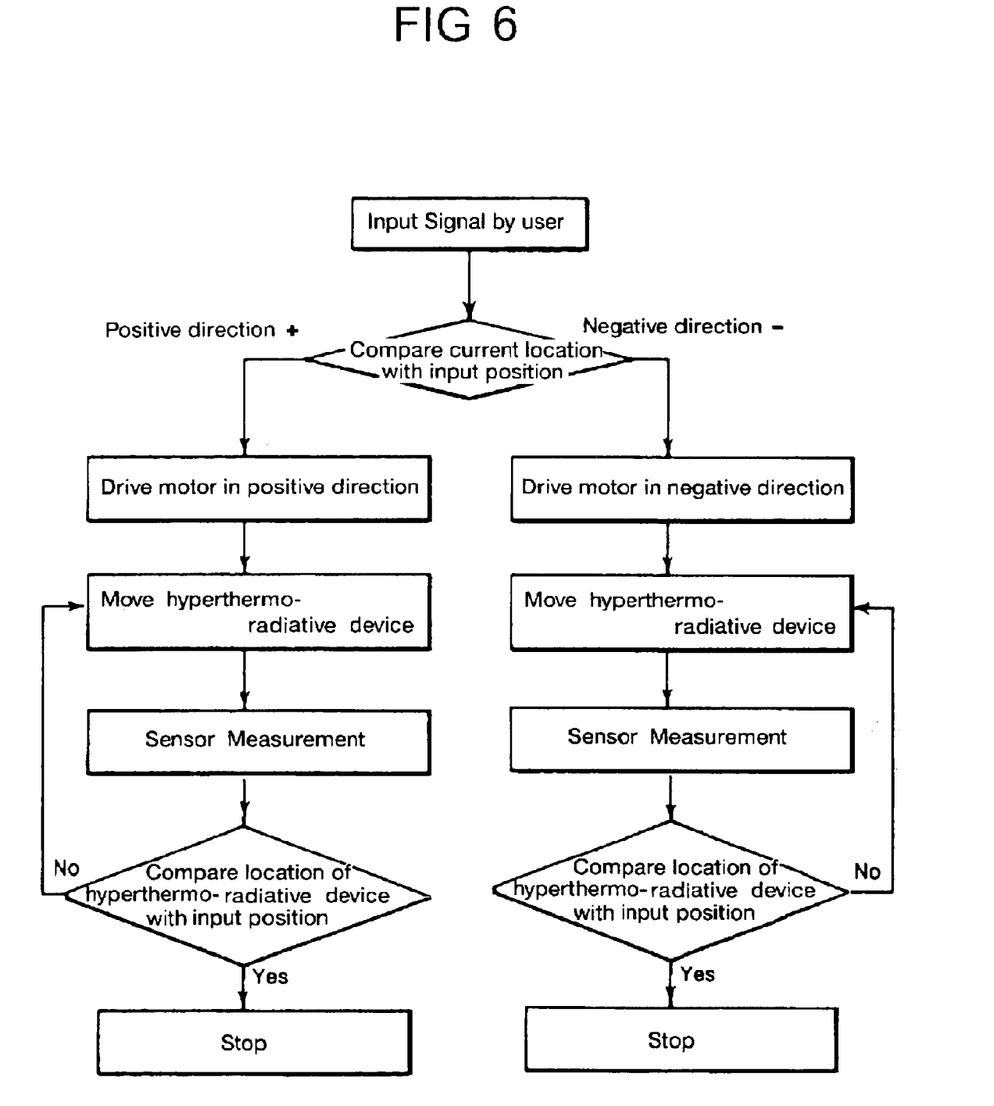
FIG. 6 is a flowchart illustrating a method of controlling the bed type hot compress and acupressure apparatus according to the present invention.

FIG. 6 is a flowchart schematically showing the method of controlling the bed type hot compress and acupressure apparatus 200 according to the present invention.

The bed type hot compress and acupressure apparatus 200 according to the present invention begins to operate when the user beforehand inputs the position of a vertebra required to be hyper thermally treated into the remote control. At first, the control unit compares a current location of the hyperthermo-radiative device 126 with the position of the vertebra that has been input by the user, and determines a direction in which the hyperthermo-radiative device 126 should be moved. At this time, if the position information that has been input by the user is not completely consistent with the current location of the hyperthermo-radiative device 126, the hyperthermo-radiative device 126 must be moved to the designated location corresponding to the position of the vertebra, this location will be a location in front of or at the rear of the hyperthermo-radiative device 126. Meanwhile, for the sake of explanation, it is more desirable to set a point of reference. In the present invention, a direction in which the hyperthermo-radiative device 126 should be moved toward the pulley 128 is defined as a positive (+) direction, whereas a direction in which the hyperthermo-radiative device 126 should be moved toward the electric-powered motor 112 is defined as a negative (−) direction, respectively.

When a direction in which the hyperthermo-radiative device 126 should be moved is determined, the electric-powered motor 112 is operated in the positive (+) or negative (−) direction. At this time, the motor shaft 114 causes the belt gear 122 and the belt member 124 to move the hyperthermo-radiative device 126 in practice. Such movement is the same as conventional hot compress and acupressure apparatuses.

Meanwhile, during the movement of the hyperthermo-radiative device 126, the means 100 for controlling a location of the hyperthermo-radiative device measures continuously and in real time a location to which the hyperthermo-radiative device 126 is actually moved and a position designated by the user by using the signal sensor unit 130, and then compares the location with the position. The comparison method will be described in detail below.

While the electric-powered motor 112 operates, a rotational force of the electric-powered motor 112 is transmitted to the rotational shaft 132 that is connected to the motor shaft 114 and the belt gear 122. The rotational shaft 132 transmits the rotating force to the signal rotating plate 134 through the belt gear 122. Since the signal rotating plate 134 and the belt gear 122 define concentric circles around the rotational shaft 132, the signal rotating plate 134 and the belt gear 122 are rotated by the same number of revolutions. As soon as the signal rotating plate 134 is stopped, the belt gear 122 is also stopped.

Meanwhile, since the signal emitting part 137a formed on one side portion of the sensor member 136 emits a predetermined signal, and the signal sensing part 137b formed on the other side portion of the sensor member 136 senses the emitted signal, the signal rotating plate 134 and the belt gear 122 are rotated continuously so far as a stop signal transmitted by the control unit has not been received or the sensed signal conforms to a signal transmitted by the control unit. Therefore, the amount of rotation and the number of revolutions of the signal rotating plate 134 are measured.

If the current location of the hyperthermo-radiative device 126 that has been actually moved differs from a set position designated by the user, the hyperthermo-radiative device 126 is moved continuously. However, if the current location of the hyperthermo-radiative device 126 is identical to the position designated by the user, the movement of the hyperthermo-radiative device 126 is stopped and hyperthermic treatment is then performed. A hyperthermic treatment time can be determined by a program or arbitrarily input by the user.

When a predetermined treatment time has passed, the position of a vertebra input by the user is compared again with the current location of the hyperthermo-radiative device 126, and the aforementioned processes are repeated.

The present invention controls the amount of rotation and the number of revolutions of the signal rotating plate 134 by means of the aforementioned method, so that the hyperthermo-radiative device 126 can be accurately moved by a required distance.

As described above, the present invention can control the rotation of the belt gear using the signal rotating plate and the sensor member. Therefore, there is an advantage in that the moving distance of the hyperthermo-radiative device can be controlled by the belt gear and the belt member on the order of millimeters.

Further, through the series of processes described above, the present invention can more accurately locate the hyperthermo-radiative device at a vertebral region (e.g., the fifth vertebra or the eighth vertebra) that is designated in advance by the user. Thus, there is an advantage that the user can more efficiently obtain the effects of hot compress and acupressure on a region desired by the user.

Although the present invention has been described in connection with the preferred embodiments of the means for controlling a location of the hyperthermo-radiative device and the bed type hot compress and acupressure apparatus using the same, the embodiments are for illustrative purposes only and the present invention is not limited thereto. The scope of the present invention is defined by the appended claims.

It will be apparent that those skilled in the art can make various changes and modifications thereto without departing from the scope and spirit of the present invention, and the changes and modifications also fall within the scope of the present invention.

What is claimed is:

1. A bed type hot compress and acupressure apparatus comprising:

a bed frame that defines an entire shape of the apparatus and has members to be assembled with one another;

a main mat and an auxiliary mat placed and mounted on the bed frame;

two curved rails mounted at a central portion within the main mat;

a controller that controls a location of a hyperthermo-radiative device such that a moving distance of the hyperthermo-radiative device can be controlled based on an actually moved distance thereof, regardless of the passage of time; and a control unit that allows a user to arbitrarily control a reciprocating device that reciprocates the hyperthermo-radiative device.

2. The apparatus as claimed in claim 1, wherein the controller that controls the location of the hyperthermo-radiative device comprises:

a reciprocating unit including a belt gear coupled to a motor shaft of an electric-powered motor to convert a rotational force of the electric-powered motor into a forward and rearward reciprocating motion, a belt member that is engaged and in contact with an outer peripheral surface of the belt gear and reciprocated forward or rearward through the belt gear, the hyperthermo-radiative device connected to the belt member to reciprocate forward and rearward, and a pulley disposed on a side opposite to the belt gear to reciprocate the belt member; and a signal sensor unit including a rotational shaft connected to the motor shaft and the belt gear to directly transmit the rotational force, a signal rotating plate rotated together with the belt gear by the rotational shaft, and a sensor member that is adjacent to both faces of the signal rotating plate to sense a signal from the signal rotating plate and transmit the sensed signal to the control unit.

3. A method of controlling a bed type hot compress and acupressure apparatus, wherein a hyperthermo-radiative device of the apparatus is reciprocated and a reciprocating motion is controlled based on a moving distance of the hyperthermo-radiative device, comprising:

comparing a current location of the hyperthermo-radiative device with a position of a vertebra input by a user, and determining a direction in which the hyperthermo-radiative device should be moved;

moving the hyperthermo-radiative device through an electric-powered motor;

measuring, by a signal sensor unit, a location to which the hyperthermo-radiative device is actually moved, during the movement of the hyperthermo-radiative device, and comparing an actually moved location of the hyperthermo-radiative device with a position designated by the user;

continuously performing the measuring if the actually moved location of the hyperthermo-radiative device differs from the position designated by the user; and stopping the movement of the hyperthermo-radiative device and performing a treatment if the location and the position are identical to each other.

4. The method as claimed in claim 3, wherein the comparing the actually moved location of the hyperthermo-radiative device with the position designated by the user further comprises:

transmitting the rotational force of the electric-powered motor to a signal rotating plate through a rotational shaft connected to a motor shaft and a belt gear, and measuring the number of revolutions and an amount of rotation of the signal rotating plate a sensor member which is adjacent to both faces of the signal rotating plate while the signal rotating plate is rotated together with the belt gear about the rotational shaft; and moving the hyperthermo-radiative device by a required distance by controlling again the number of revolutions and the amount of rotation of the signal rotating plate measured in the measuring.

* * * * *

UNITED STATES PATENT AND TRADEMARK OFFICE
CERTIFICATE OF CORRECTION

PATENT NO. : 6,952,614 B2  Page 1 of 1
APPLICATION NO. : 10/757436
DATED : October 4, 2005
INVENTOR(S) : S. U. Choi It is certified that error appears in the above-identified patent and that said Letters Patent is hereby corrected as shown below:

Column 10,
Line 31, after "plate" insert -- by --.

Signed and Sealed this

Twentieth Day of June, 2006

JON W. DUDAS
*Director of the United States Patent and Trademark Office*